(12) United States Patent
Wollrab et al.

(10) Patent No.: US 9,150,475 B2
(45) Date of Patent: Oct. 6, 2015

(54) PROCESS FOR PRODUCING ETHANOL BY HYDROGENATION WITH CARBON MONOXIDE CONTROLS

(71) Applicant: Celanese International Corporation, Irving, TX (US)

(72) Inventors: Radmila Wollrab, Pasadena, TX (US); Iva Franjkic, League City, TX (US); Victor J. Johnston, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 14/075,177

(22) Filed: Nov. 8, 2013

(65) Prior Publication Data

US 2015/0133700 A1  May 14, 2015

(51) Int. Cl.
  *C07C 67/08* (2006.01)
  *C07C 29/151* (2006.01)

(52) U.S. Cl.
  CPC .................................. *C07C 29/1512* (2013.01)

(58) Field of Classification Search
  CPC .................................................... A01B 12/006
  USPC ........................................................ 568/884
  See application file for complete search history.

(56) References Cited

U.S. PATENT DOCUMENTS

| | | | |
|---|---|---|---|
| 2,882,244 A | 4/1959 | Milton | |
| 3,130,007 A | 4/1964 | Breck | |
| 4,242,875 A | 1/1981 | Schaefer | |
| 4,497,967 A | 2/1985 | Wan | |
| 4,756,730 A | 7/1988 | Stupin | |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,511,382 A | 4/1996 | Denis et al. | |
| 5,599,976 A | 2/1997 | Scates et al. | |
| 6,143,930 A | 11/2000 | Singh et al. | |
| 6,509,180 B1 | 1/2003 | Verser et al. | |
| 6,627,770 B1 | 9/2003 | Cheung et al. | |
| 6,657,078 B2 | 12/2003 | Scates et al. | |
| 6,927,048 B2 | 8/2005 | Verser et al. | |
| 7,005,541 B2 | 2/2006 | Cheung et al. | |
| 7,074,603 B2 | 7/2006 | Verser et al. | |
| 7,115,772 B2 | 10/2006 | Picard et al. | |
| 7,208,624 B2 | 4/2007 | Scates et al. | |
| 7,351,559 B2 | 4/2008 | Verser et al. | |
| 7,507,562 B2 | 3/2009 | Verser et al. | |
| 7,601,865 B2 | 10/2009 | Verser et al. | |
| 7,608,744 B1 | 10/2009 | Johnston et al. | |
| 7,682,812 B2 | 3/2010 | Verser et al. | |
| 7,863,489 B2 | 1/2011 | Johnston et al. | |
| 7,888,082 B2 | 2/2011 | Verser et al. | |
| 7,923,405 B2 | 4/2011 | Kharas et al. | |
| 8,080,693 B2 | 12/2011 | Chornet et al. | |
| 8,304,586 B2 | 11/2012 | Jevtic et al. | |
| 8,304,587 B2 | 11/2012 | Warner et al. | |
| 8,309,772 B2 | 11/2012 | Weiner et al. | |
| 8,309,773 B2 | 11/2012 | Jevtic et al. | |
| 8,350,886 B2 | 1/2013 | Horihata et al. | |
| 8,450,535 B2 | 5/2013 | Johnston et al. | |
| 8,455,702 B1 | 6/2013 | Zhou et al. | |
| 8,501,652 B2 | 8/2013 | Johnston et al. | |
| 8,502,001 B2 | 8/2013 | Daniel et al. | |
| 2007/0003477 A1 | 1/2007 | Haik-Beraud et al. | |
| 2008/0193989 A1 | 8/2008 | Verser et al. | |
| 2009/0281354 A1 | 11/2009 | Mariansky et al. | |
| 2009/0318573 A1* | 12/2009 | Stites et al. | 518/700 |
| 2010/0030001 A1 | 2/2010 | Chen et al. | |
| 2010/0030002 A1 | 2/2010 | Johnston et al. | |
| 2012/0010422 A1 | 1/2012 | Stepp et al. | |
| 2012/0010438 A1 | 1/2012 | Lee et al. | |
| 2012/0010441 A1* | 1/2012 | Jevtic et al. | 568/885 |
| 2012/0149949 A1 | 6/2012 | Weiner et al. | |
| 2012/0273338 A1 | 11/2012 | Lee et al. | |
| 2012/0277490 A1 | 11/2012 | Lee et al. | |
| 2012/0277497 A1 | 11/2012 | Lee et al. | |
| 2013/0137906 A1 | 5/2013 | Jevtic et al. | |
| 2013/0211152 A1 | 8/2013 | Jevtic et al. | |

FOREIGN PATENT DOCUMENTS

| | | |
|---|---|---|
| EP | 0167300 | 1/1986 |
| EP | 2060553 | 5/2009 |

* cited by examiner

*Primary Examiner* — Yevegeny Valenrod
*Assistant Examiner* — Blaine G Doletski
(74) *Attorney, Agent, or Firm* — Kilpatrick Townsend & Stockton LLP

(57) ABSTRACT

A process for produce ethanol by hydrogenation acetic acid and/or esters thereof is disclosed. The process involves reacting hydrogen feed stream with an acetic acid feed stream in a reactor operated in the presence of a catalyst to form an ethanol mixture and monitoring carbon monoxide concentration of the fresh hydrogen feed stream and adjusting temperature in the reactor in response to the carbon monoxide concentration of the fresh hydrogen feed stream.

20 Claims, 2 Drawing Sheets

PROCESS FOR PRODUCING ETHANOL BY HYDROGENATION WITH CARBON MONOXIDE CONTROLS

FIELD OF THE INVENTION

The present invention relates generally to processes for producing and/or purifying ethanol and, in particular, to processes for producing ethanol from the hydrogenation of acetic acid and/or esters thereof and controlling the temperature of the reactor in response to the carbon monoxide concentrations of the fresh hydrogen feed streams.

BACKGROUND OF THE INVENTION

Ethanol production by hydrogenation of acetic acid and/or esters thereof is an alternative to fermentation from starchy materials or cellulosic materials. A hydrogen source is required for this ethanol production. U.S. Pat. No. 4,497,967 uses a substantially pure hydrogen source, which includes inert diluents such as carbon dioxide, nitrogen, and methane, for converting aliphatic acetates to ethanol. To obtain substantially pure hydrogen, the hydrogen must be purified from the other components, which typically includes carbon monoxide. Several processes are known to obtain hydrogen from syngas, i.e., a mixture of hydrogen and carbon monoxide. Cryogenic purification is widely used to separate syngas as described in U.S. Pat. Nos. 5,511,382, 4,756,730, and 4,242,875, the entire contents and disclosures of which are hereby incorporated by reference. Another hydrogen separation is described in US Pub. No. 2007/0003477 for purifying a gaseous flow containing at least hydrogen, carbon monoxide, a metal carbonyl, and at least one impurity selected from oxygen, and unsaturated hydrocarbons. One problem in producing pure hydrogen and carbon monoxide streams is that the energy intensive separation. The presence of additional gases, such as nitrogen and methane, may further increase the energy requirements for separation. Also, the complexity of the purification process is dependent on the desired purity of the carbon monoxide and hydrogen.

Ethanol production processes having integrated hydrogen separation techniques. EP2060553 describes a process for the conversion of a carbonaceous feedstock to ethanol, wherein the carbonaceous feedstock is first converted to ethanoic acid, which is then hydrogenated and converted into ethanol. At least part of the hydrogen stream emanates from the syngas generation procedure.

U.S. Pat. No. 8,502,001 describes a process for the conversion of ethanoic acid into ethanol by (a) introducing ethanoic acid and $H_2$ into a primary hydrogenation unit in the presence of a precious metal-based catalyst to produce ethanol and ethyl ethanoate and (b) introducing ethyl ethanoate, from step (a), together with $H_2$ into a secondary hydrogenation unit in the presence of a copper-based catalyst to produce ethanol. Ethanol from step (b) is recovered.

U.S. Pat. No. 8,080,693 describes a process for converting methanol to ethanol which comprises reacting methanol and carbon monoxide in the presence of a catalyst to produce a product comprising at least 25 mole % methyl acetate and, in some instances, acetic acid. The acetic acid then is reacted with at least one alcohol to produce at least one acetate selected from methyl acetate, ethyl acetate, and butyl acetate. The at least one acetate (if produced) and the methyl acetate produced as a result of reacting methanol and carbon monoxide then are hydrogenated to produce ethanol. Syngas may be produced from biomass to produce all or a portion of the methanol, hydrogen, and carbon monoxide requirements for the process. Carbon monoxide and hydrogen that are employed in the process are each obtained from syngas and may be separated using membranes.

EP0167300 discloses a process for the production of an aliphatic alcohol having at least two carbon atoms, preferably ethanol, from a carbonaceous feedstock, preferably natural gas, via an intermediate aliphatic alcohol having one less carbon atom, preferably methanol, via an intermediate compound containing the group $CH_3(CH_2)_nC(O)$—, preferably acetic acid. The feedstock is reformed and the synthesis gas formed is separated, preferably by a PSA unit, into three different streams which are used in the three stage process, one of which streams is a pure hydrogen stream that is used for reacting the intermediate compound to form the desired aliphatic alcohol.

Therefore, a need remains for improving the hydrogen feed stream and increasing production of ethanol.

SUMMARY OF THE INVENTION

In a first embodiment, the present invention relates to processes for producing ethanol comprising reacting hydrogen feed stream with an acetic acid feed stream in a reactor operated in the presence of a catalyst to form an ethanol mixture, separating a vapor stream from the ethanol mixture and a liquid stream from the ethanol mixture, wherein the vapor stream has a steady state concentration of carbon monoxide, recovering ethanol from the liquid stream, combining a fresh hydrogen stream and the vapor stream to form the hydrogen feed stream, and monitoring carbon monoxide concentration of the fresh hydrogen feed stream and adjusting temperature in the reactor in response to the carbon monoxide concentration of the fresh hydrogen feed stream. The fresh hydrogen stream may comprise from 0.03 to 1.5 mol. % carbon monoxide, e.g., from 0.5 to 1 mol. % carbon monoxide, and preferably is substantially free of carbon dioxide, nitrogen, methane, and ethane. The steady state concentration of carbon monoxide in the vapor stream may be less than 2 mol. %. The vapor stream further comprises carbon dioxide, nitrogen, methane, ethane, or mixtures thereof. Carbon monoxide in excess of the steady state concentration of carbon monoxide in the vapor stream may be dissolved in the liquid stream. In one embodiment, the process may comprise purging less than 15% of the vapor stream. In another embodiment, the process may comprise combining a secondary purified hydrogen stream with the fresh hydrogen stream and the vapor stream to form the hydrogen feed stream, wherein the secondary purified hydrogen stream contains at least 99.99 mol. % hydrogen.

In a second embodiment, the present invention relates to processes for producing ethanol comprising reacting hydrogen feed stream with an acetic acid feed stream in a reactor operated in the presence of a catalyst to form an ethanol mixture, separating a vapor stream from the ethanol mixture and a liquid stream from the ethanol mixture, wherein the vapor stream has a steady state concentration of carbon monoxide, recovering ethanol from the liquid stream, combining a fresh hydrogen stream that contains carbon monoxide and is less than 99.99% and the vapor stream to form the hydrogen feed stream, and monitoring carbon monoxide concentration of the fresh hydrogen feed stream and adjusting the reactor to a temperature that is greater than 270° C., preferably from 270° C. to 305° C., when the carbon monoxide concentration of the fresh hydrogen feed stream exceeds 0.03 mol. %, preferably from 0.03 mol. % to 1.5 mol. %. In one embodiment, the process may comprise purging less than 15% of the vapor stream. In another embodiment, the process may comprise combining a secondary purified hydrogen stream with the fresh hydrogen stream and the vapor stream to form the hydrogen feed stream, wherein the secondary purified hydrogen stream contains at least 99.99 mol. % hydrogen.

In another embodiment, the present invention also relates to a process for producing an ethanol mixture comprises providing a fresh hydrogen feed stream comprising hydrogen and from 0.03 to 1.5 mol. % carbon monoxide and reacting the hydrogen feed stream with an acetic acid feed stream in a reactor operated at a temperature of at least 270° C. in the presence of a catalyst to form the ethanol mixture. The process further comprises flashing a vapor stream from the ethanol mixture, and recovering ethanol from a liquid portion of the ethanol mixture and recycling the vapor stream to the reactor wherein carbon monoxide concentration in the vapor stream is equal to or less than the hydrogen feed stream. The process further comprises purging less than 15% of the vapor stream.

In another embodiment, the present invention further relates to a process for producing the ethanol mixture comprises reacting the hydrogen feed stream with an acetic acid feed stream in a reactor operated in the presence of a catalyst to form the ethanol mixture. The process further comprises flashing a vapor stream from the ethanol mixture and recovering ethanol from a liquid portion of the ethanol mixture. The process further comprises monitoring carbon monoxide concentration of the hydrogen feed stream and operating the reactor at a temperature of greater than 270° C. when the carbon monoxide concentration exceeds 0.1 mol. %.

In yet another embodiment, the process comprises monitoring carbon monoxide concentration of the hydrogen feed stream and purging the vapor stream when the carbon monoxide concentration exceeds 0.1 mol. % and introducing a purified hydrogen feed stream containing at least 99.99 mol. % hydrogen.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
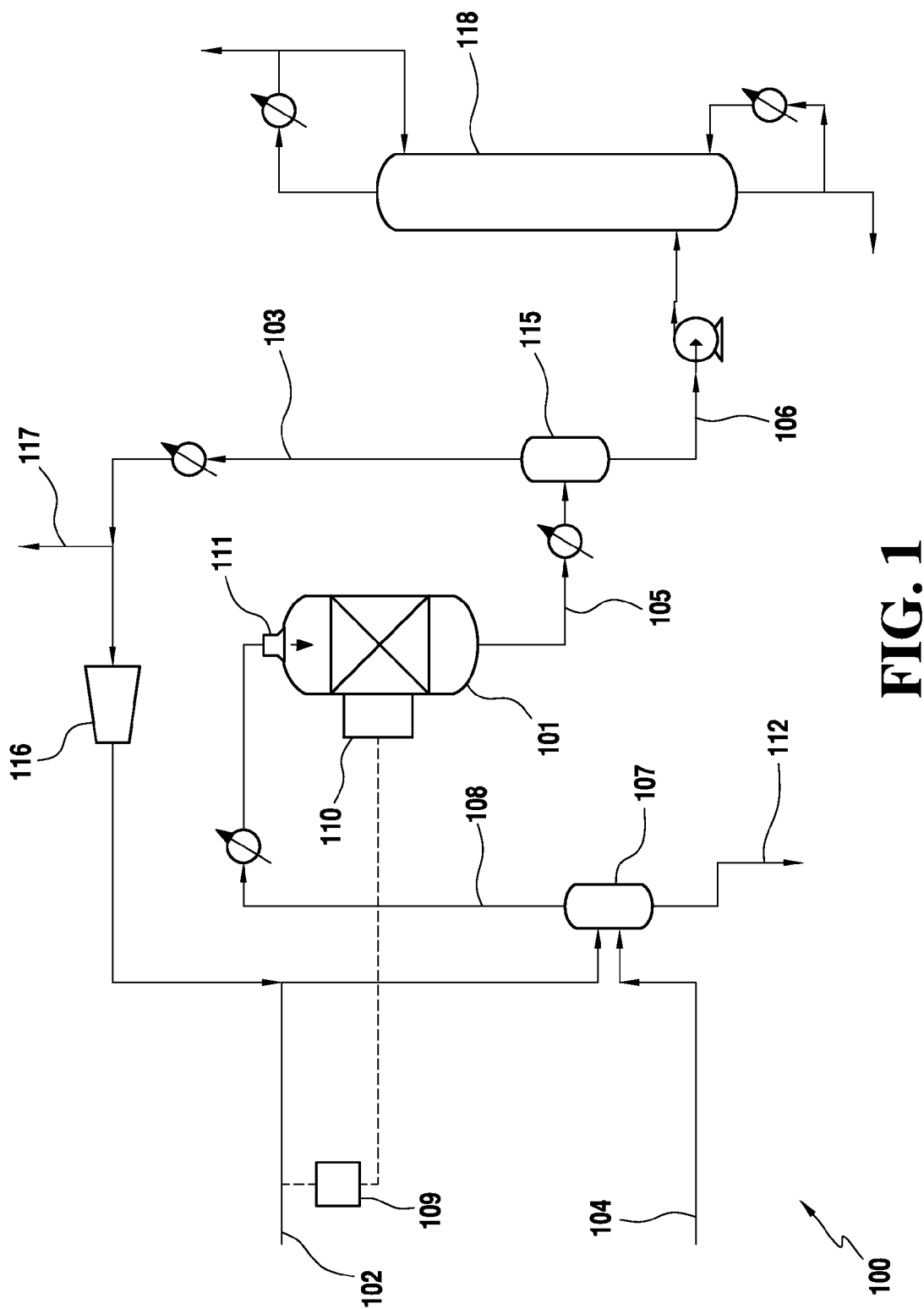
FIG. 1 is a schematic diagram of the reaction zone in accordance with one embodiment of the present invention.

The present invention relates to processes for producing ethanol by a hydrogenation process comprising hydrogenating acetic acid and/or esters thereof in the presence of a catalyst. In particular, the present invention relates to controlling the hydrogenation reactor based on the concentration of carbon monoxide in the fresh hydrogen stream. Embodiments of the present invention beneficially may be used in applications for hydrogenating acetic acid and/or esters thereof to produce ethanol on an industrial scale.

Carbon monoxide is known to be poisonous to hydrogenation catalysts and therefore, the uncontrolled buildup of carbon monoxide would negatively affect the conversion of acetic acid and/or esters thereof to ethanol. Carbon monoxide may be present in the hydrogenation reactor due to impurities in the fresh hydrogen stream or due to decomposition of other components during the hydrogenation of acetic acid and/or esters thereof that build up when recycled to the reactor. The decomposition of other components is difficult to inhibit, and carbon monoxide may be formed under a wide variety of conditions and catalysts. In addition, the recycle streams typically contain a steady state concentration of carbon monoxide. As the reaction effluent is withdrawn from the reactor and condensed, the recycled vapor stream has a steady state concentration of carbon monoxide and the excess carbon monoxide is dissolved into the liquid stream. Steady state concentration of carbon monoxide refers to the amount of carbon monoxide that is in the vapor stream and not dissolved. Other byproduct gases, such as carbon dioxide, nitrogen, methane, and ethane, may also reach a steady state concentration in the vapor recycle stream. Typically this amount reaches a steady state in a continuous hydrogenation process after a few hours on stream. For purposes of the present invention, the steady state concentration of carbon monoxide in the vapor stream may be less than 2 mol. %, e.g., less than 1 mol. % or less than 0.5 mol. %. In terms of ranges, the vapor stream may contain from 0.001 mol. % to 2 mol. % carbon monoxide, e.g., from 0.005 mol. % to 1 mol. % or from 0.01 mol. % to 0.5 mol. %. In addition, in some embodiments, a portion of the vapor stream, typically less than 15%, may be purged to control impurities, including but not limited to carbon monoxide. Due to the dissolved carbon monoxide and/or purging of the vapor stream, monitoring the concentration of carbon monoxide in the recycle stream alone may not provide sufficient information regarding the carbon monoxide concentration in the reactor.

To provide improved control of the hydrogenation reaction and improve ethanol productivity, the present invention monitors carbon monoxide concentration of the fresh hydrogen feed stream and adjusts temperature in the reactor in response to the carbon monoxide concentration of the fresh hydrogen feed stream. A fresh hydrogen feed stream may be needed to maintain reactor pressure and the desired hydrogen to acetic acid and/or ester molar ratio. Fresh hydrogen feed stream refers to a source of hydrogen that has not passed over a hydrogenation catalyst. In one embodiment, the fresh hydrogen stream is substantially free of carbon dioxide, nitrogen, methane, and ethane. The fresh hydrogen feed stream may be a pure hydrogen stream containing 99.99 mol. % hydrogen. The pure hydrogen stream is also substantially free of carbon dioxide, nitrogen, methane, and ethane, and in addition may also be substantially free of carbon monoxide. In other embodiments, depending on the source of hydrogen and method to purify the hydrogen, the fresh hydrogen feed stream may contain from 0.03 to 1.5 mol. % carbon monoxide, e.g., from 0.5 to 1 mol. % carbon monoxide, and from 98.5 to 99.97 mol. % hydrogen, e.g., from 99 to 99.5 mol. % hydrogen. Relatively higher amounts of carbon monoxide in the fresh hydrogen feed stream may allow the present invention to use a variety hydrogen sources and may reduce the purification requirements.

In response to the monitored carbon monoxide concentration in the fresh hydrogen feed stream, the present invention adjusts the temperature of the reactor. Hydrogenation may be conducted a temperature from 125° C. to 350° C., and lower temperatures are preferred to reduce energy consumption. Advantageously increasing the reaction temperature may suppress the poisoning effects of the carbon monoxide and maintain ethanol production. The increased reaction temperature may tolerate higher levels of carbon monoxide. The temperature response to the monitored carbon monoxide may be done in real-time or in near real-time. In one embodiment, when the monitored carbon monoxide concentration is greater than 0.03 mol. %, the reaction temperature may be increased to a temperature of greater than 270° C., e.g., greater than 280° C., or greater than 290° C. The temperature may be adjusted by increasing the operating temperature at least 5° C., e.g., at least 10° C., or at least 20° C. For example, when the operating temperature is 280° C. and a carbon monoxide concentration of greater than 0.03 mol. % is measured in the fresh hydrogen feed stream, then the reaction temperature may be increased to at least 285° C., preferably from 285° C. to 350° C. Additionally, when the operating temperature is 250° C. and a carbon monoxide concentration of greater than 0.03 mol. % is measured in the fresh hydrogen feed stream, then the reaction temperature may be increased to at least 270° C., preferably from 270° C. to 350° C.

For purposes of the present invention, the reaction temperature is the average temperature across the catalyst bed. Each reactor may have one or more heaters. Exemplary reactors may have from 4 to 12 heaters. The heaters may be internal or external, such as a jacketed heater. Pre-heating of the feed to the reactor may also be used to control the reaction temperature. In addition, the reactor may have one or more thermocouples for monitoring the reactor temperature. The thermocouples may be located adjacent to each of the heaters as well as adjacent to the inlet and outlet. One or more of these heaters may be controlled to adjust the temperature. To handle the increased carbon monoxide that is fed to the reactor, it may be preferred to adjust the inlet temperature or heaters near the inlet.

When the concentration of carbon monoxide in the fresh hydrogen feed stream is less than 0.02 mol. %, i.e. when pure hydrogen is used, the reactor temperature may be restored to a lower operating temperature. Advantageously the affect of the increased carbon monoxide is a reversible catalyst poison that may achieve substantially the same conversion and selectivity. A pure hydrogen stream may be used, as needed, to dilute the fresh hydrogen feed stream and to lower the operating reactor temperature.

For purposes of the present invention, any suitable instrument may be used to monitor the concentration of vapor stream gases, such as: hydrogen, methane, ethane, carbon monoxide, and carbon dioxide. This may include but is not limited to on-line gas chromatography, mass spectrometry, GC/MS, on-line infrared spectroscopy, infrared gas analyzer, near infrared (NIR), FT-NIR, ultra-violet radiation analyzer, visible radiation analyzer, LED analyzer, or tunable diode laser analyzers laser. The concentration of acetic acid may also be monitored prior to combining the fresh hydrogen feed stream with the recycled vapor stream.

In some embodiments, the concentration of carbon monoxide in the recycled vapor stream may also be monitored and used in combination with the fresh hydrogen measurement to control the reaction temperature.

As stated above, using hydrogen sources that are less pure and contain from 0.03 to 1.5 mol. % carbon monoxide may reduce the separation needed when hydrogen is obtained from gasification, steam or carbon dioxide reforming, autothermal reforming, or as waste gas from other chemical processes. Generally these methods produce hydrogen and carbon monoxide. In addition, a less pure hydrogen source may allow further integration of the process, and in particular for integration gasification process with hydrogenation processes. In one embodiment, the integrated process may involve producing ethanol from a carbon source to ethanol by converting the carbon source to syngas, separating a portion of the syngas into a hydrogen stream and a carbon monoxide stream, carbonylating methanol with the carbon monoxide stream to form acetic acid, and reducing the acetic acid with the hydrogen stream to form ethanol. In addition, the syngas or the hydrogen stream and carbon monoxide stream may be reacted over a rhodium catalyst to produce methanol. In another embodiment, the integrated process may involve producing ethanol from a carbon source to ethanol by converting the carbon source to syngas, separating a portion of the syngas into a hydrogen stream and a carbon monoxide stream, carbonylating methanol with the carbon monoxide stream to form acetic acid, esterifying the acetic acid to form ethyl acetate, and reducing the ethyl acetate with the hydrogen stream to form ethanol. In other embodiments, the acetic acid may be first reduced to ethyl acetate as an alternative to esterification.

The carbon source may include natural gas, petroleum, coal, biomass, and combinations thereof. In one embodiment, the natural gas may be stranded natural gas or associated gas, i.e. natural gas that is often in remote locations that make recovery and delivery to markets cost prohibitive. The hydrogenation reactor may be co-located with gasification unit that converts the stranded natural gas or associated gas to syngas. Examples of biomass include, but are not limited to, agricultural wastes, forest products, grasses, and other cellulosic material, timber harvesting residues, softwood chips, hardwood chips, mixtures of softwood and hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, grape seeds, almond shells, pecan shells, coconut shells, coffee grounds, grass pellets, hay pellets, wood pellets, cardboard, paper, plastic, cloth, forest residue, paper mill waste, including sludge and plastics, willow, alfalfa, pelletized refuse derived fuel, bagasse, California highway clippings, and mixtures thereof.

Preferably acetic acid is obtained from methanol carbonylation and integrated with the hydrogen separation as discussed above. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259 and 4,994,608, the entire disclosures of which are incorporated herein by reference. In other embodiments, the acetic acid may be obtained from acetaldehyde oxidation, ethane oxidation, oxidative fermentation, and anaerobic fermentation. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Depending on the source of acetic acid, the acetic acid fed to the hydrogenation reaction may also comprise other carboxylic acids, esters, and anhydrides, as well as acetaldehyde and acetone. Preferably, a suitable acetic acid feed stream comprises acetic acid and one or more of the compounds selected from the group consisting of acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed in amounts up to 15 wt. %, e.g., up to 10 wt. %. In some embodiments, the acetic acid feed stream may contain mixtures of ethyl acetate and acetic acid, e.g., from 5 to 95 wt. % acetic acid and from 5 to 95 wt. % ethyl acetate or preferably from 40 to 95 wt. % acetic acid and from 5 to 60 wt. % ethyl acetate. In other embodiments, a ethyl acetate stream comprising more than 95 wt. % ethyl acetate may be reduced to form ethanol.

When molar excess of hydrogen, regardless of carbon monoxide concentrations, is used to reduce the acetic acid feed stream, thermal decomposition of acetic acid, water-gas shift reaction and ethanol dehydration occur and form undesirable by-products, such as methane, ethane, carbon monoxide and carbon dioxide (Formulas I-IV):

$$CH_3COOH \rightarrow CH_4 + CO_2 \quad \text{I}$$

$$CO_2 + H_2 \leftrightarrow CO + H_2O \quad \text{II}$$

$$CH_3CH_2OH \rightarrow CH_2=CH_2 + H_2O \quad \text{III}$$

$$CH_2=CH_2 + H_2 \rightarrow CH_3CH_3 \quad \text{IV}$$

The by-product gases are recycled to the reactor with the hydrogen. The recycled vapor stream comprises hydrogen, carbon monoxide, carbon dioxide, nitrogen, methane, ethane, or mixtures thereof. The by-product gases may be harmful to certain types of hydrogenation catalysts and may lead decrease catalyst performance and to the formation of further impurities in the ethanol. As needed by-product gases may be purged, but purging results in a loss of hydrogen. The level of by-product gases in the reactor reaches a steady state as the hydrogen gas is recycled. Without being bound by theory, at the steady state concentrations the by-product gases are dissolved in the liquid phase and may be vented after separation in one or more columns. Thus, hydrogen may be effectively recycled while some of the excess by-product gases may be removed from the process without a loss of hydrogen.

Turning now to FIG. 1, there is provided a hydrogenation system comprising a reaction zone 100 of a suitable for the hydrogenation of acetic acid and/or ester thereof to form ethanol according to one embodiment of the present invention. Reaction zone 100 comprises a reactor 101, fresh hydrogen feed stream 102, vapor stream 103, and acetic acid feed stream 104. Hydrogenation system further comprises a purification zone (not shown) for recovering ethanol, as described further herein. As provided herein the concentration of carbon monoxide may vary in fresh hydrogen feed stream 102. Fresh hydrogen feed stream 102 may comprise from 0.03 to 1.5 mol. % carbon monoxide, e.g., from 0.5 to 1 mol. % carbon monoxide, and from 98.5 to 99.97 mol. % hydrogen, e.g., from 99 to 99.5 mol. % hydrogen. In some embodiments, fresh hydrogen feed stream 102 may be a pure hydrogen stream containing greater than 99.99 mol. % hydrogen. Fresh hydrogen feed stream 102, vapor stream 103, and acetic acid feed stream 104 fed to reactor 101 to form a crude ethanol product stream 105.

Although the reaction consumes two moles of hydrogen per mole of acetic acid to produce one mole of ethanol, the actual molar ratio of hydrogen to acetic acid in the feed stream may vary from 100:1 to 4:1, e.g., from 50:1 to 4:1, from 20:1 to 4:1, or from 12:1 to 4:1. Most preferably, the molar ratio of hydrogen to acetic acid is greater than 4:1, e.g., greater than 6:1 or greater than 8:1. The molar ratio may be maintained through feeding fresh hydrogen feed stream 102.

Vapor stream 103 is obtained from crude ethanol product stream 105 and returned to reactor 101. The composition of vapor stream 103 may varied depending on the by-product reactions and purges. In some embodiments, carbon monoxide concentrations may be decreased in vapor stream 103 by passing a portion of vapor stream over a methanation catalyst as described in US Pub. No. 2013/0137906, the entire contents and disclosure of which is hereby incorporated by reference. In an exemplary embodiment, vapor stream 103 may comprise unreacted hydrogen in an amount from 90 to 100 mol. %, e.g., 92 to 98 mol. %, or 93 to 97 mol. % and contains by-product gases in an amount less than 10 mol. %, e.g., less than 5 mol. %, or less than 1 mol. %. In one embodiment, the by-product gases are selected from the group consisting of methane, ethane, carbon dioxide, carbon monoxide, nitrogen, and mixtures thereof. Generally, the by-product gases, when present, are present in steady state concentrations. Carbon monoxide concentration in the vapor stream may be from 0.001 to 2 mol. %, e.g., 0.005 to 0.3 mol. %, or 0.01 to 0.2 mol. %. Methane concentration may be from 0.001 to 3 mol. %, e.g., 0.005 to 1.5 mol. % or 0.01 to 1.2 mol. %. Ethane concentration may be from 0.001 to 3 mol. %, e.g., 0.005 to 1 mol. % or 0.01 to 0.8 mol. %. Carbon dioxide concentration may be from 0.001 to 3 mol. %, e.g., from 0.005 to 0.8 mol. % or from 0.001 to 0.5 mol. %. Nitrogen concentrations may vary depending on the acetic acid feed stream 104, and typically nitrogen concentration are less than 2 mol. %.

When recovering vapor stream 103, a liquid stream 106 is also obtained from crude ethanol product stream 105 and liquid stream 106 may be further processed in purification zone (not shown) to recover ethanol.

The flow ratio of fresh hydrogen in hydrogen feed stream 102 to hydrogen in vapor stream 103 is from 1:1 to 1:20, e.g., from 1:1 to 10, or from 1:1 to 1:8. Generally, there is more hydrogen on a flow basis in vapor stream 103 than in hydrogen feed stream 102. To control the amount of fresh hydrogen supplied to the hydrogenation system, the fresh hydrogen may be controlled using supply-side pressure regulation or offgas-side pressure regulation. In one embodiment, the pressure in the reactor is measured and is kept constant by means of a regulator that acts on the supply device for the fresh hydrogen. Offgas-side pressure regulation controls the amount of replacement fresh hydrogen, a fixed amount of fresh hydrogen is fed into the reactor and the reactor pressure is kept constant by means of a regulator that acts on the offgas valve of the recycled vapor stream.

As shown in FIG. 1, fresh hydrogen feed stream 102, vapor stream 103, and acetic acid feed stream 104 are fed to a vaporizer 107 to produce a vapor feed stream 108. Although the hydrogenation reaction may be conducted in the liquid or gas phase, the gas phase is preferred. To control the temperature in the hydrogenation reaction, an analyzer 109 monitors the concentration of carbon monoxide in fresh hydrogen feed stream 102. Analyzer 109, such as those described herein, may operate in real-time or near real-time. When carbon monoxide concentration exceeds 0.3 mol. %, e.g., from 0.3 to 1.5 mol. %, in fresh hydrogen feed stream 102 a controller (not shown), such as a distributed control system (DCS) or a programmable logic controller (PLC), outputs a response signal to one or more heaters 110. As shown in FIG. 1, heaters 110 are external heaters. A thermocouple may also be used to measure temperature in reactor 101 and provide feedback temperature information to the controller. In one embodiment, there may be multiple controllers for various components of the system. Vapor feed stream 108 enters reactor 101 through inlet 111 and contacts the catalyst contained therein to hydrogenate the acetic acid and/or ester thereof. Although inlet 111 is shown on the top of reactor 101 in FIG. 1, in other embodiments inlet 111 may be located on the side, upper portion or bottom of reactor 101. In addition, there may be one or more inlets 111 for each reactor 101.

For reactions run in the vapor phase, the temperature should be controlled in vaporizer 107 such that the temperature does not fall below the dew point of acetic acid. In one embodiment, the acetic acid may be vaporized at the boiling point of acetic acid at the particular pressure, and fed along with hydrogen from the fresh hydrogen feed stream 102 and vapor stream 103 in an undiluted state or diluted with a relatively inert carrier gas, such as nitrogen, argon, helium, carbon dioxide and the like. The temperature of vapor feed stream 108 is preferably from 100° C. to 350° C., e.g., from 120° C. to 310° C. or from 150° C. to 300° C. Any feed that is not vaporized is removed from vaporizer 107, via blowdown 112.

In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Acetic acid feed stream 104 may be preheated to a temperature of at least 40° C., e.g., at least 70° C. or at least 85° C., prior to being fed to vaporizer 107. Fresh hydrogen feed stream 102 may also be preheated to a temperature of at least 40° C., e.g., at least 70° C. or at least 85° C., prior to being fed to vaporizer 107.

In one embodiment, one or more guard beds (not shown) may be used upstream of the reactor 101, optionally upstream of vaporizer 107, to protect the catalyst from poisons or undesirable impurities contained in the feed or return/recycle streams. These guard beds are not sufficient for protecting the catalyst from carbon monoxide. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

Reactor 101 may include a variety of configurations, such as a fixed bed reactor or a fluidized bed reactor. In other embodiments, a radial flow reactor or reactors may be employed, or a series of reactors may be employed with heat exchange, quenching, or introduction of additional feed material. Alternatively, a shell and tube reactor provided with a heat transfer medium may be used. In many cases, the reaction zone may be housed in a single vessel or in a series of vessels with heat exchangers there between.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C., if the carbon monoxide concentration in fresh hydrogen feed stream 102 is less than 0.03 mol. %. When the carbon monoxide concentration in fresh hydrogen feed stream 102 is greater than 0.03 mol. %, the temperature may be controlled to range from 270° C. to 350° C., e.g., from 280° C. to 350° C., or from 290° C. to 350° C. The pressure may range from 10 kPa to 3000 kPa, e.g., from 100 kPa to 2700 kPa, or from 100 kPa to 2300 kPa. The reactants may be fed to the reactor at a gas hourly space velocity (GHSV) ranging from 50 $hr^{-1}$ to 50,000 $hr^{-1}$, e.g., from 1000 $hr^{-1}$ to 10,000 $hr^{-1}$, or from 1000 $hr^{-1}$ to 6500 $hr^{-1}$.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactants through the catalyst bed and the contact time of the reactant compounds with the catalyst particles.

Reactor 101 contains the catalyst that is used in the hydrogenation of the acetic acid and/or ester thereof. The hydrogenation of acetic acid to form ethanol is preferably conducted in the presence of one or more hydrogenation catalysts. Exemplary hydrogenation catalysts may include, but are not limited to, platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, rhodium/tin, silver/palladium, copper/palladium, copper/zinc, nickel/palladium, gold/palladium, ruthenium/rhenium, and ruthenium/iron on a suitable support. Exemplary catalysts are further described in U.S. Pat. Nos. 7,608,744, 7,863,489, 8,309,772, 8,350,886, 8,450,535, 8,455,702, and 8,501,652 and U.S. Pub. No. 2013/0211152, the entireties of which are incorporated herein by reference. In another embodiment, the catalyst comprises a Co/Mo/S catalyst of the type described in U.S. Pat. No. 7,923,405, the entirety of which is incorporated herein by reference. In one embodiment, the hydrogenation catalyst may be combined with copper-based catalyst, such as a copper-zinc or a copper-chromium catalyst, in a stack-bed as described in US Pub. No. 2012/0149949, the entirety of which is incorporated herein by reference.

In one embodiment, the hydrogenation catalyst comprises a Group VIII metal and at least one other second metal on a support. The Group VIII metal may be present in the catalyst in an amount from 0.1 to 10 wt. %, e.g., from 0.1 to 5 wt. %, or from 0.1 to 3 wt. %. In one embodiment, when the Group VIII metal is cobalt, iron or nickel, the loading may be up to 25 wt. %, e.g., from 0.1 to 25 wt. %. The second metal preferably is present in an amount from 0.1 to 25 wt. %, e.g., from 0.1 to 10 wt. %, or from 0.1 to 5 wt. %. The hydrogenation catalyst may comprise a metal selected from the group consisting of iron, cobalt, nickel, rhodium, palladium, osmium, iridium, and platinum. Preferably, the Group VIII metal is selected from the group consisting of platinum, palladium, cobalt, and rhodium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

The catalyst further comprises a second metal, which typically would function as a promoter. Suitable second metal may be selected from the group consisting of copper, molybdenum, tin, chromium, iron, cobalt, vanadium, tungsten, lanthanum, cerium, manganese, gold, and nickel. More preferably, the second metal is selected from the group consisting of copper, tin, cobalt, molybdenum, and tungsten. Most preferably, the second metal is selected from tin and cobalt. In some embodiments, there may one or more second metals on the catalyst. For examples, the catalyst may comprise cobalt and tin, molybdenum and tin, tungsten and tin, or cobalt and tungsten in addition the Group VIII metal.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. The support modifier may be present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, or $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

Exemplary hydrogenation catalyst may include the following. Platinum (0.5 to 3 wt. %) and tin (0.5 to 5 wt. %) on silica. Cobalt (3 to 25 wt. %) and tin (3 to 25 wt. %) on silica. Platinum (0.5 to 3 wt. %) and tin (0.5 to 5 wt. %) on calcium metasilicate. Platinum (0.5 to 3 wt. %) and cobalt (0.5 to 5 wt. %) on silica. Cobalt (1 to 25 wt. %) and tin (1 to 25 wt. %) on silica. Rhodium (0.5 to 3 wt. %) and tin (0.5 to 5 wt. %) on silica. Platinum (0.5 to 3 wt. %) and tin (0.5 to 5 wt. %) on silica modified with $CaSiO_3$ (1 to 10 wt. %). Platinum (0.5 to 3 wt. %), tin (0.5 to 10 wt. %), and cobalt (0.5 to 10 wt. %) on silica modified with $CaSiO_3$ (1 to 10 wt. %). Rhodium (0.5 to 3 wt. %), tin (0.5 to 10 wt. %), and cobalt (0.5 to 10 wt. %) on silica modified with $CaSiO_3$ (1 to 10 wt. %). Platinum (0.5 to 3 wt. %), tin (0.5 to 10 wt. %), and cobalt (0.5 to 10 wt. %) on silica modified with $WO_3$ (1 to 20 wt. %). Platinum (0.5 to 3 wt. %), tin (0.5 to 10 wt. %), and cobalt (0.5 to 10 wt. %) on silica modified with $CoWO_4$ (1 to 20 wt. %). Platinum (0.5 to 3 wt. %), tin (0.5 to 10 wt. %), and cobalt (0.5 to 10 wt. %) on silica modified with tin and $CoWO_4$ (1 to 20 wt. %). Platinum (0.5 to 3 wt. %) and tin (0.5 to 10 wt. %) on silica modified with tin and $CoWO_4$ (1 to 20 wt. %). Platinum (0.5 to 3 wt. %) and tin (0.5 to 10 wt. %) on silica modified with $WO_3$ (1 to 20 wt. %). Other hydrogenation catalyst described herein may also be used with embodiments of the present invention. In addition, other supports described herein may also be used.

The hydrogenation catalysts suitable for use with the present invention preferably are formed through metal impregnation of the modified support, although other processes such as chemical vapor deposition may also be employed. Such impregnation techniques are described in U.S. Pat. Nos. 7,608,744, 7,863,489 and 8,501,652 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments, a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the hydrogenation process, before any subsequent processing, such as purification and separation, will typically comprise unreacted acetic acid, ethanol and water. Exemplary component ranges for the crude ethanol product are provided in Table 1. Other components, such as, for example, alcohols, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %.

TABLE 1

CRUDE ETHANOL PRODUCT COMPOSITIONS

| Component | Conc. (wt. %) | Conc. (wt. %) | Conc. (wt. %) | Conc. (wt. %) |
| --- | --- | --- | --- | --- |
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

The crude ethanol product may be condensed and fed to flasher 115, which, in turn, creates vapor stream 103 and a liquid stream 106. The flasher 115 in one embodiment preferably operates at a temperature from 20° C. to 250° C., e.g., from 30° C. to 225° C. or from 60° C. to 200° C. In one embodiment, the pressure of flasher 115 preferably is from 50 to 2000 kPa, e.g., from 75 to 1500 kPa or from 100 to 1000 kPa. In some embodiments, there may be two flashers, a high pressure flasher and low pressure flasher in series. Vapor stream 103 may be taken from the high pressure flasher. In one preferred embodiment the temperature and pressure of flasher 115 is similar to the temperature and pressure of reactor 101. Ethanol produced from reactor 101 can be recovered from the liquid stream 109.

As described above, vapor stream 103 may be returned to reactor 101. When vapor stream 103 is returned to reactor 101 it may be necessary to increase the pressure and vapor stream 103 is passed through one or more compressors 116. Prior to compressing, one or more purge streams 117 may be taken to remove build up of by-product gases. In one embodiment, purge stream 117 is less than 15% of the vapor stream, e.g., less than 10% or less than 1%.

In addition, there may be one or more analyzers (not shown) for monitoring the by-products in vapor stream 103.

As stated above, by-product gases, such as methane, ethane, carbon monoxide, carbon dioxide, and/or nitrogen, may be dissolved in liquid stream 106 exiting flasher 115. Depending on the solubility limit of the by-product gas or mixtures of gases, the concentration of the dissolved by-product gases may vary. The solubility of a gas in a liquid depends on temperature, the partial pressure of the gas over the liquid, the nature of the liquid and the nature of the gas.

In one embodiment, the dissolved by-product gases, such as methane, ethane, carbon monoxide, carbon dioxide and/or nitrogen, in a concentration from 0.00001 to 0.1 wt. %, e.g., 0.0001 to 0.01 wt. % or 0.001 to 0.005 wt. %. Liquid stream 106 may be further separated to recover ethanol. The dissolved by-product gases may be vented as needed.

As shown in FIG. 1, liquid stream 106 is fed to one or more distillation column 118 to recover ethanol from the crude ethanol product. Although one distillation column is shown, it is understood that multiple distillation columns may be used to remove organic impurities and water. Ethanol separation processes suitable for use with the present invention are described in U.S. Pat. Nos. 8,309,773, 8,304,586, 8,304,587 and US Pub. Nos. 2012/0010438, 2012/0010422, 2012/0273338, 2012/0277490, 2012/0277497, the entire disclosures of which are incorporated herein by reference. In addition to distillation columns there may be one or more water separator to further dehydrate the recovered ethanol. Water separator units may include adsorption unit, membrane, molecular sieves, extractive column distillation, or a combination thereof. For example, water separator may be a pressure swing adsorption unit.

The columns shown in FIG. 1, may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in FIG. 1, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Without being bound by theory, the effect of carbon monoxide on hydrogenation catalyst is understood to be a reversible poison so that the catalyst is able to achieve substantially similar performance in terms of conversion, selectivity, and/or productivity once a fresh hydrogen feed stream that is pure hydrogen is used. In particular, is able to achieve substantially similar performance at the previous reduced temperature. For purposes of reversible catalyst, substantially similar performance means that the performance after carbon monoxide exposure is no less than 5% than the performance prior to carbon monoxide exposure, e.g., no less than 2%. When a carbon monoxide is present in an amount of greater than 0.3 mol. % in the fresh hydrogen feed stream the catalyst performance is expected to decrease and the temperature in the reactor is increased to offset the expected decrease. Once pure hydrogen is fed as the fresh hydrogen feed stream, the catalyst achieve substantially similar performance in tennis of conversion, selectivity, and/or productivity. For example, using a hydrogen catalyst, the conversion prior to carbon monoxide exposure may be 95% and during increase carbon monoxide exposure the conversion may decrease to 90% despite increasing the temperature. Once pure hydrogen is used, then the reactor temperature may be decreased, and the catalyst performance in teens of conversion is greater than 90.5%.

Figure 2:
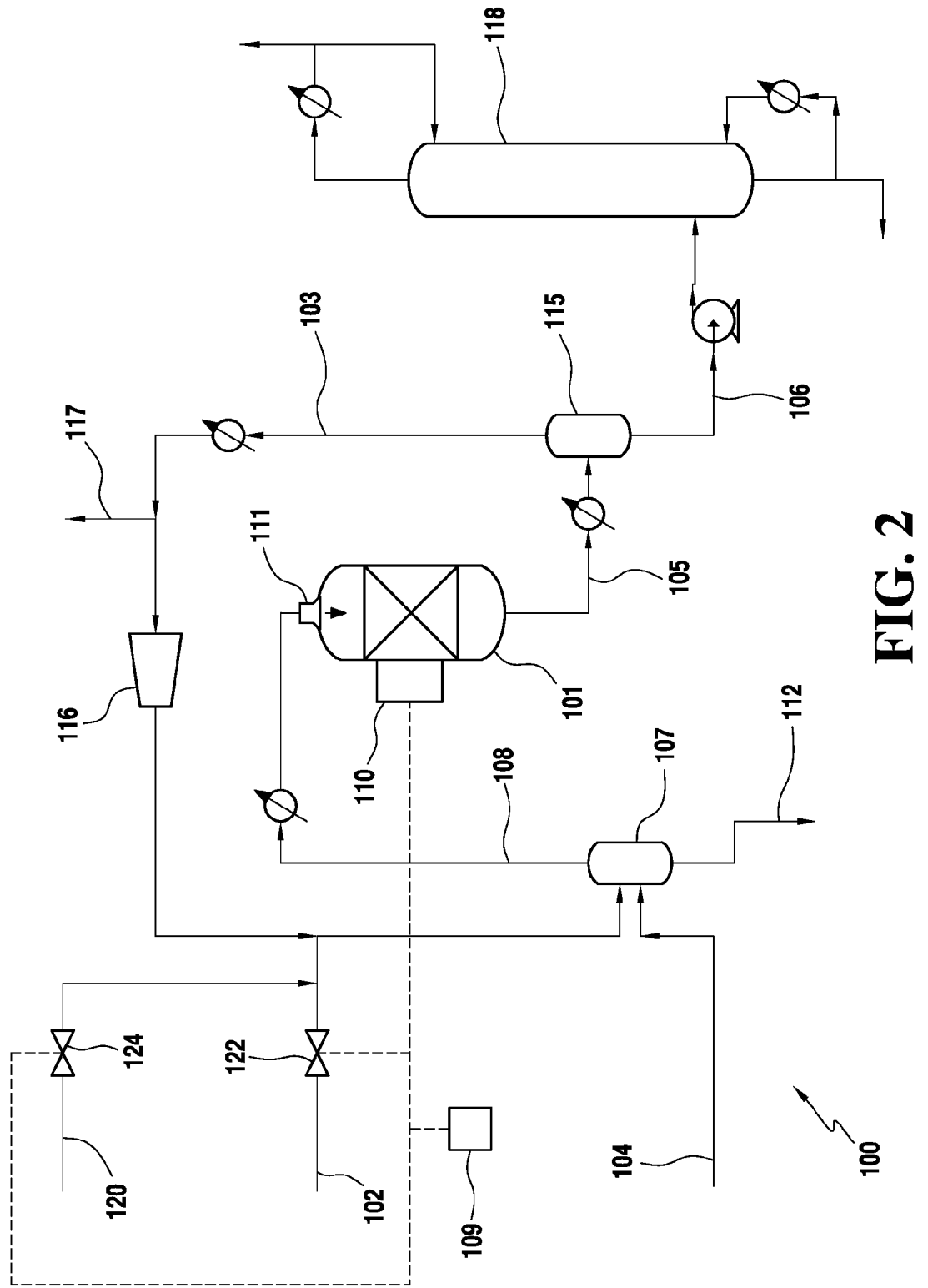
FIG. 2 is a schematic diagram of the reaction zone having two sources of fresh hydrogen in accordance with one embodiment of the present invention.

As shown in FIG. 2, there is a second hydrogen feed stream 120 that contains pure hydrogen, e.g., greater than 99.99 mol. % hydrogen. Second hydrogen feed stream 120 is also a fresh hydrogen source. The carbon monoxide concentration in hydrogen feed stream 102 is monitored as described herein and when carbon monoxide concentrations increase, the controller changes the reactor temperature. In addition, in FIG. 2, the controller may also control valves 122 and 124 to regulate the flow between hydrogen feed stream 102 that may contain carbon monoxide and second hydrogen feed stream 120 that contains pure hydrogen. To monitor the purity of second hydrogen feed stream 120 a separate analyzer (not shown) may be used.

Also to restore a pure hydrogen feed and low reactor temperature, valve 124 may be opened and valve 122 closed to allow a pure hydrogen feed to be used a fresh hydrogen feed stream.

The final ethanol product by the present invention is obtained from the purification zone. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 2.

TABLE 2

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 2, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including application as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882, 244 and zeolite Y in U.S. Pat. No. 3,130,007, the entireties of which are hereby incorporated herein by reference.

In order that the invention disclosed herein may be more efficiently understood, an example is provided below. The following examples describe the various distillation processes of the present invention.

EXAMPLES

Example 1

A system was setup to measure the conversion of acetic acid. The hydrogenation catalyst used was $SiO_2(CaSi_2O_3)$(6 wt. %)-Pt(1.8 wt. %)Sn(3.5 wt. %). The pressure for the conversion reaction was set at about 2,070 kPa. The acetic acid flow rate was set at 3.56 mL/min acetic acid. Varying amounts of carbon monoxide were tested to determine the poisoning effects on the catalyst. Three runs with the following amounts of carbon monoxide tested were: 0.04 wt. %, 0.15 wt. %, and 1.0 wt. %. Prior to each run with carbon monoxide there was a run with pure hydrogen (greater than 99.99 mol. %). Additionally, the temperature was varied to determine if the temperature change affected the conversion rate of acetic acid in the presence of carbon monoxide. Table 3 shows the % of converted acetic acid under the varying conditions.

TABLE 3

CONVERSION OF ACETIC ACID

| Run | CO (wt. %) | 225° C. | 250° C. | 275° C. | 300° C. |
|---|---|---|---|---|---|
| 1 (w/pure H$_2$) | — | 16.4% | 26.3% | 39.7% | 53.2% |
| 1 | 0.04 | 13.1% | 22.7% | 37.2% | 52.5% |
| 2 (w/pure H$_2$) | — | 18.5% | 29.4% | 43.3% | 56.4% |
| 2 | 0.15 | 10.9% | 22.5% | 38.7% | 54.3% |
| 3 (w/pure H$_2$) | — | 17.6% | 28.2% | 41.6% | 55.3% |
| 3 | 1 | 5.2% | 12.5% | 26.9% | 44.0% |

Example 2

A system similar to Example 1 was setup to measure the conversion of acetic acid. The hydrogenation catalyst used was SiO$_2$(CoWO$_4$) (10 wt. %)-Pt (1 wt. %) Sn (4 wt. %). The pressure for the conversion reaction was set at about 2,070 kPa. The acetic acid flow rate was set at 3.56 mL/min acetic acid. Varying amounts of carbon monoxide were tested to determine the poisoning effects on the catalyst. One run with different amounts of carbon monoxide was tested: 0.15 wt. %, and 1 wt. %. Prior to feeding the carbon monoxide, a run with pure hydrogen was tested. Additionally, the temperature was varied to determine if the temperature change affected the conversion rate of acetic acid in the presence of carbon monoxide. Table 4 shows the % of converted acetic acid under the varying conditions.

TABLE 4

CONVERSION OF ACETIC ACID

| Run | CO (wt. %) | 225° C. | 250° C. | 275° C. |
|---|---|---|---|---|
| 4 (w/pure H$_2$) | — | 66.3% | 87.8% | 92.5% |
| 4 | 0.15 | 46.9% | 78.5% | 92.1% |
| 4 | 1 | 30.1% | 68.2% | 90.3% |

Table 4 shows that increased temperature at 275° C., the presence of carbon monoxide has only a small effect on the conversion of acetic acid.

Example 3

Using the same catalyst and reaction conditions from example 2, except the temperature of the reaction was increased above 270° C. Prior to increasing the amount of carbon monoxide in the reaction, the conversion rate of acetic acid was approximately 98%. For 100 hours, carbon monoxide (from 0.15 to 1 mol. % CO) was added to the reaction. After 100 hours, the carbon monoxide was removed and the conversion of acetic acid returned to approximately 98% at a lower temperature than 270° C. This indicates that the increased temperature and carbon monoxide poisoning is reversible.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol comprising:
    reacting hydrogen feed stream with an acetic acid feed stream in a reactor operated in the presence of a catalyst to form an ethanol mixture;
    separating a vapor stream from the ethanol mixture and a liquid stream from the ethanol mixture, wherein the vapor stream has a steady state concentration of carbon monoxide;
    recovering ethanol from the liquid stream;
    combining a fresh hydrogen stream and the vapor stream to form the hydrogen feed stream; and
    monitoring carbon monoxide concentration of the fresh hydrogen feed stream and adjusting temperature in the reactor in response to the carbon monoxide concentration of the fresh hydrogen feed stream.

2. The process of claim 1, wherein the fresh hydrogen stream comprises from 0.03 to 1.5 mol. % carbon monoxide.

3. The process of claim 1, wherein the fresh hydrogen stream comprises from 0.5 to 1 mol. % carbon monoxide.

4. The process of claim 1, wherein the hydrogen feed stream is substantially free of carbon dioxide, nitrogen, methane, and ethane.

5. The process of claim 1, further comprising combining a sufficient amount of the fresh hydrogen stream to maintain a molar ratio of hydrogen in the hydrogen feed stream to acetic acid in the acetic acid feed stream in the reactor of greater than 4:1.

6. The process of claim 1, wherein the steady state concentration of carbon monoxide in the vapor stream is less than 2 mol. %.

7. The process of claim 1, wherein the vapor stream further comprises carbon dioxide, nitrogen, methane, ethane, or mixtures thereof.

8. The process of claim 1, wherein the reactor has a concentration of carbon monoxide that is greater than the steady state concentration of carbon monoxide in the vapor stream.

9. The process of claim 1, wherein carbon monoxide in excess of the steady state concentration of carbon monoxide in the vapor stream is dissolved in the liquid stream.

10. The process of claim 1, wherein the adjusted temperature is greater than 270° C. when the carbon monoxide concentration of the fresh hydrogen stream exceeds 0.03 mol. %.

11. The process of claim 1, wherein the adjusted temperature is from 270° C. to 305° C. when the carbon monoxide concentration of the fresh hydrogen stream is from 0.03 mol. % to 1.5 mol. %.

12. The process of claim 1, wherein the adjusted temperature is from 290° C. to 305° C. when the carbon monoxide concentration of the fresh hydrogen stream is from 1 mol. % to 1.5 mol. %.

13. The process of claim 1, further comprising purging less than 15% of the vapor stream.

14. The process of claim 1, wherein the ethanol mixture comprises less than 10 wt. % acetic acid.

15. The process of claim 1, further comprising combining a secondary purified hydrogen stream with the fresh hydrogen stream and the vapor stream to form the hydrogen feed stream, wherein the secondary purified hydrogen stream contains at least 99.99 mol. % hydrogen.

16. A process for producing ethanol comprising:
    reacting hydrogen feed stream with an acetic acid feed stream in a reactor operated in the presence of a catalyst to form an ethanol mixture;

separating a vapor stream from the ethanol mixture and a liquid stream from the ethanol mixture, wherein the vapor stream has a steady state concentration of carbon monoxide;

recovering ethanol from the liquid stream;

combining a fresh hydrogen stream that contains carbon monoxide and is less than 99.99% and the vapor stream to form the hydrogen feed stream; and monitoring carbon monoxide concentration of the fresh hydrogen feed stream and adjusting the reactor to a temperature that is greater than 270° C. when the carbon monoxide concentration of the fresh hydrogen feed stream exceeds 0.03 mol. %.

17. The process of claim 16, further comprising combining a sufficient amount of the fresh hydrogen stream to maintain a molar ratio of hydrogen in the hydrogen feed stream to acetic acid in the acetic acid feed stream in the reactor of greater than 4:1.

18. The process of claim 16, wherein the steady state concentration of carbon monoxide in the vapor stream is less than 2 mol. %.

19. The process of claim 16, further comprising purging less than 15% of the vapor stream.

20. The process of claim 16, further comprising combining a secondary purified hydrogen stream with the fresh hydrogen stream and the vapor stream to form the hydrogen feed stream, wherein the secondary purified hydrogen stream contains at least 99.99 mol. % hydrogen.

* * * * *